United States Patent
Curtis

(10) Patent No.: US 10,117,982 B2
(45) Date of Patent: Nov. 6, 2018

(54) SYSTEM AND METHOD FOR IMPROVING A HEART MUSCLE RESPONSE

(71) Applicant: Guy P. Curtis, San Diego, CA (US)

(72) Inventor: Guy P. Curtis, San Diego, CA (US)

(73) Assignee: Guy P. Curtis and Frances L. Curtis Trust CA (US)

( * ) Notice: Subject to any disclaimer, the term of this patent is extended or adjusted under 35 U.S.C. 154(b) by 155 days.

(21) Appl. No.: 15/099,975

(22) Filed: Apr. 15, 2016

(65) Prior Publication Data

US 2017/0296724 A1  Oct. 19, 2017

(51) Int. Cl.

| A61M 1/12 | (2006.01) |
|---|---|
| A61M 1/10 | (2006.01) |
| A61B 5/021 | (2006.01) |
| A61B 5/0215 | (2006.01) |
| A61B 5/00 | (2006.01) |
| A61M 5/142 | (2006.01) |

(52) U.S. Cl.
CPC ......... *A61M 1/1086* (2013.01); *A61B 5/0215* (2013.01); *A61B 5/02141* (2013.01); *A61B 5/4836* (2013.01); *A61B 5/6853* (2013.01); *A61M 1/106* (2013.01); *A61M 1/1075* (2014.02); *A61M 5/142* (2013.01)

(58) Field of Classification Search
CPC .................................................. A61M 1/1074
See application file for complete search history.

(56) References Cited

U.S. PATENT DOCUMENTS

| 3,412,729 A | 11/1968 | Smith, Jr. | |
|---|---|---|---|
| 4,861,330 A * | 8/1989 | Voss ...................... | A61M 1/122 600/18 |
| 4,902,273 A * | 2/1990 | Choy ..................... | A61M 1/122 600/18 |
| 5,423,746 A | 6/1995 | Burkett et al. | |
| 5,971,932 A | 10/1999 | Okamoto | |
| 6,406,422 B1 | 6/2002 | Landesberg | |
| 6,468,243 B1 | 10/2002 | Miyagawa et al. | |
| 6,511,413 B2 * | 1/2003 | Landesberg ........ | A61M 1/1046 600/16 |
| 7,300,404 B1 | 11/2007 | Kolluri et al. | |
| 2002/0052621 A1 | 5/2002 | Fried et al. | |
| 2004/0059183 A1 | 3/2004 | Jansen et al. | |
| 2007/0287880 A1 * | 12/2007 | Ovil ..................... | A61M 1/1074 600/16 |
| 2010/0087744 A1 | 4/2010 | Licata | |
| 2011/0021911 A1 | 1/2011 | Waters et al. | |

FOREIGN PATENT DOCUMENTS

WO  2008154643 A1  12/2008

\* cited by examiner

*Primary Examiner* — George Evanisko

(74) *Attorney, Agent, or Firm* — Nydegger & Associates

(57) ABSTRACT

A system for improving heart muscle response during a pre-ejection phase in the heart muscle pumping cycle requires a catheter having a pressure transducer and a fluid device mounted at its distal end. Also included is a pump connected to the proximal end of the catheter in fluid communication with the fluid device. A computer will activate the pump in response to a predetermined signal from the pressure transducer to inject and maintain an increased fluid volume in the pumping chamber of the heart for a predetermined time interval $\Delta t$ during the pre-ejection phase. This supplements the isometric pressure in the heart's pumping chamber in preparation for a subsequent ejection of blood from the pumping chamber.

10 Claims, 3 Drawing Sheets

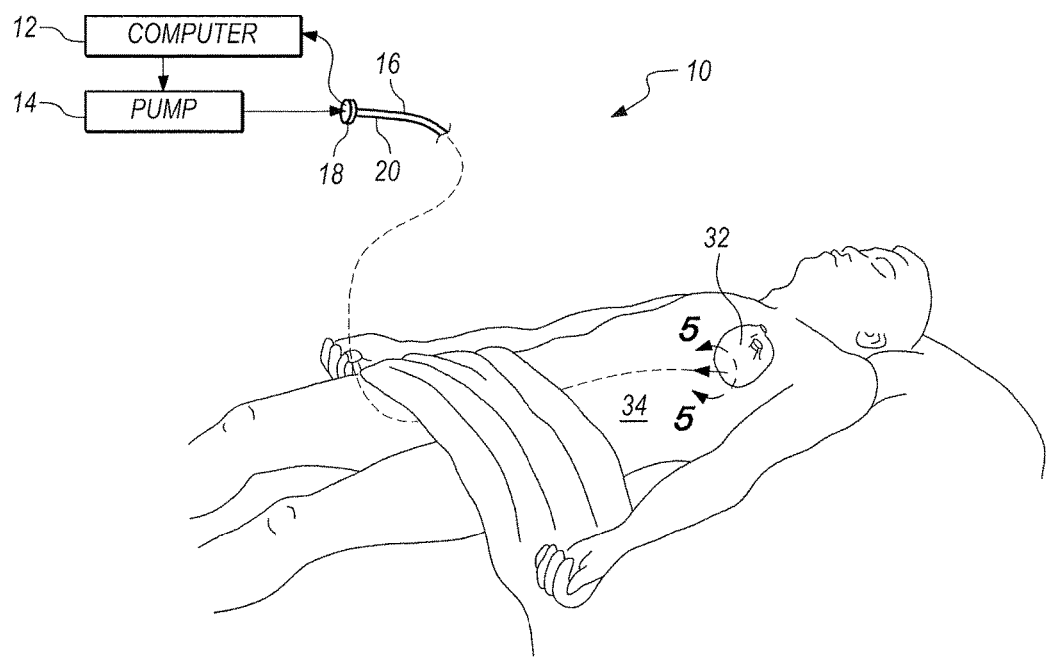
FIG. 1
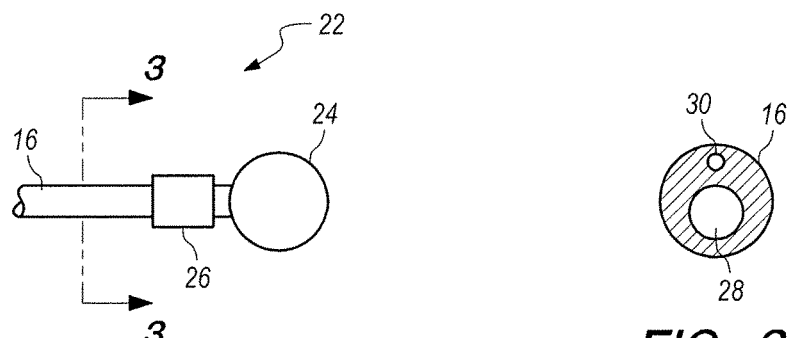
FIG. 2
FIG. 3

SYSTEM AND METHOD FOR IMPROVING A HEART MUSCLE RESPONSE

FIELD OF THE INVENTION

The present invention pertains generally to systems and methods for improving a heart muscle function. More particularly, the present invention pertains to systems and methods that improve the pumping action of the heart's left ventricle. The present invention is particularly, but not exclusively, useful for improving the heart muscle function by mechanically supplementing isometric pressure in the pumping chamber of the left ventricle during the pre-ejection phase of the heart pumping cycle, to thereby improve the heart's ability to eject blood from the chamber.

BACKGROUND OF THE INVENTION

During a heart muscle pumping cycle, which normally lasts for about 500 msec, there is a phase wherein the pumping chamber of the heart (i.e. the left ventricle) is completely enclosed. In this phase, known as the pre-ejection phase, the chamber has been filled with blood, and both the inlet valve and the outlet valve of the chamber are closed. Thus, during the pre-ejection phase, which lasts around 10 msec, the chamber (left ventricle) remains essentially isovolumic.

Anatomically, the heart muscle exerts pressure on blood in the chamber during the pre-ejection phase for two fundamentally different purposes. One is to first increase pressure in the chamber to a point where the outlet valve of the left ventricle will open. Essentially this is accomplished by contractile elements in the heart muscle which will exert an isometric pressure on blood in the chamber during the pre-ejection phase. The other is to eject the blood from the chamber, post pre-ejection phase, after the outlet valve of the chamber has been opened. This ejection of blood is accomplished by series-elastic elements of the heart muscle that shorten to effectively squeeze blood from the chamber through the open outlet valve.

From a mechanical perspective, because they must necessarily overlap somewhat during the pre-ejection phase, the combined action of the contractile and series-elastic elements of the heart muscle is two-fold. In tandem, the contractile elements initially exert an isometric pressure on the blood. This is preparatory to a subsequent, more efficient, ejection of blood from the chamber by the series-elastic elements. In this combination there is a balance between the two functions that will provide for a most efficient heart muscle contraction. Importantly, this balance needs to be established and maintained during the entire pre-ejection phase.

The beginning of the pre-ejection phase occurs when both the inlet and outlet valves of the chamber have been closed, and isometric pressure on blood in the chamber is initiated. It is an abrupt, sudden increase in isometric pressure that is characteristic of the beginning of the pre-ejection phase. From a metric standpoint, the abrupt, sudden increase in pressure at the beginning of the pre-ejection phase is detectable as a pressure discontinuity. Operationally, this pressure discontinuity is useable as a start point for employing mechanical techniques that will improve heart function during the pre-ejection phase.

With a weakened heart, which may result from any number of different reasons, the heart's ability to exert an isometric pressure during the pre-ejection phase is the first function to diminish its efficacy. The resultant imbalance in the application of forces on the heart's pumping chamber is detrimental to heart function. Consequently, the need to maintain an operational balance between the isometric pressure that is needed to open the chamber outlet valve, and providing the forces that are necessary for actually ejecting blood from the chamber, is essential for an efficiently operating heart.

In light of the above, it is an object of the present invention to provide a system and method for improving a heart muscle function that establishes and maintains a balance between isometric pressure on the pumping chamber of the heart during the pre-ejection phase, and the subsequent forces on the heart that eject blood from the pumping chamber. Another object of the present invention is to provide a system and method for improving heart muscle function by mechanically assisting in the preparation of a heart muscle contraction during the pre-ejection phase of a heart muscle pumping cycle. Still another object of the present invention is to provide a system for improving heart muscle function that is easy to manufacture, is simple to use and is comparatively cost effective.

SUMMARY OF THE INVENTION

In accordance with the present invention, a system and a method for improving heart muscle function are provided. Specifically, the system is provided to supplement isometric pressure on blood within the pumping chamber of the left ventricle (i.e. the chamber) during the pre-ejection phase of the heart muscle's pumping cycle. Operationally, this is done to improve the efficacy of the heart's ability to subsequently pump blood from the chamber. As intended for the present invention, supplementation of this isometric pressure in the chamber will be repetitively provided, on a continuing basis, during a succession of heart muscle cycles. Moreover, this will continue for as long as is determined to be necessary by the attending physician. As envisioned for the present invention, its use will be primarily in an Intensive Care Unit (ICU) or a Cath Lab.

Structurally, a system in accordance with the present invention includes a catheter with a fluid device and a pressure transducer. Both the fluid device and the transducer are mounted at the distal end of the catheter. Also included in the system is a fluid pump that is connected to the proximal end of the catheter. Importantly, the pump is connected to the catheter for fluid communication with the fluid device. A computer is also included which is connected to both the pump and the pressure transducer.

For purposes of the present invention the fluid device will preferably be an inflatable balloon made of a compliant material, and it will have an inflated volume that is in an approximate range between 2 cc and 7 cc when it is fully inflated. A liquid solution (e.g. saline) is used for inflation and deflation of the balloon. For the present invention, the inflation and deflation of the balloon are accomplished in a computer-controlled operation. Another component of the present invention, the pressure transducer, is preferably of a type that is well known in the pertinent art, such as a Millar Mikro-Tip® pressure transducer.

In an alternate embodiment of the present invention, instead of an inflatable balloon, the fluid device may be an injection tube. For this alternate embodiment, the injection tube will be an elongated hollow needle that is formed with an end cap. A plurality of side ports are formed along the length of the needle and, similar to the preferred embodiment, an injection of fluid from the injection tube (like inflation of the balloon) is accomplished in a computer-controlled operation.

For an operation of the present invention, the distal end of the catheter, along with the fluid device, (either the inflatable balloon or the injection tube), and the pressure transducer, are inserted into the pumping chamber of the heart. Initially, for the preferred embodiment, the balloon is collapsed. The computer, which is connected with the pressure transducer, will then monitor pressure on blood in the chamber. In response to a predetermined signal from the pressure transducer, which is indicative of the beginning of the pre-ejection phase, the computer will activate the pump for pressurizing the balloon or ejecting fluid from the injection tube. In particular, the predetermined signal from the pressure transducer is an abrupt and sudden, natural increase in pressure on blood inside the pumping chamber which characterizes the beginning of the pre-ejection phase of the heart pumping cycle. As indicated above, in the pre-ejection phase the pumping chamber of the heart remains essentially isovolumic.

For the preferred embodiment of the present invention, once the signal is received from the pressure transducer, the computer initiates a pressurization of the balloon that continues for at least a predetermined time interval $\Delta t$. Because the pumping chamber is isovolumic during the pre-ejection phase, i.e. during the time interval $\Delta t$, the balloon will exert an isometric force on blood in the pumping chamber. Specifically, this is done in order to supplement the naturally occurring isometric pressure in the chamber during the pre-ejection phase. In the event, once the supplemented isometric pressure reaches a certain pressure level, the outlet valve of the heart's pumping chamber will open and blood starts to be ejected from the chamber. Accordingly, at the end of the pre-ejection phase, the balloon can then be deflated.

As described above, the operational sequence of computer-controlled actions for a preferred embodiment of the present invention will include: 1) monitoring pressure on blood in the chamber; 2) pressurizing the balloon in response to a predetermined signal; 3) maintaining pressure in the balloon prior to ejection of blood from the chamber; and 4) deflating the balloon after the ejection of blood from the pump begins. This cycle can be subsequently repeated. Indeed, the operational sequence can be repeated as many times as is necessary to improve the heart muscle function.

For the alternate embodiment of the present invention, when the predetermined signal is received from the pressure transducer, the computer causes the pump to inject a predetermined amount of fluid from the injection tube directly into the pumping chamber of the heart muscle. As with the preferred embodiment, this injection of fluid is done at the beginning of the heart's pre-ejection phase.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 1 is a schematic view of a system of the present invention shown in its intended operational environment;

FIG. 2 is a plan view of the distal tip of a catheter in accordance with the present invention;

FIG. 3 is a cross-section view of the catheter as seen along the line 3-3 in FIG. 2;

DESCRIPTION OF THE PREFERRED EMBODIMENTS

Figure 4:
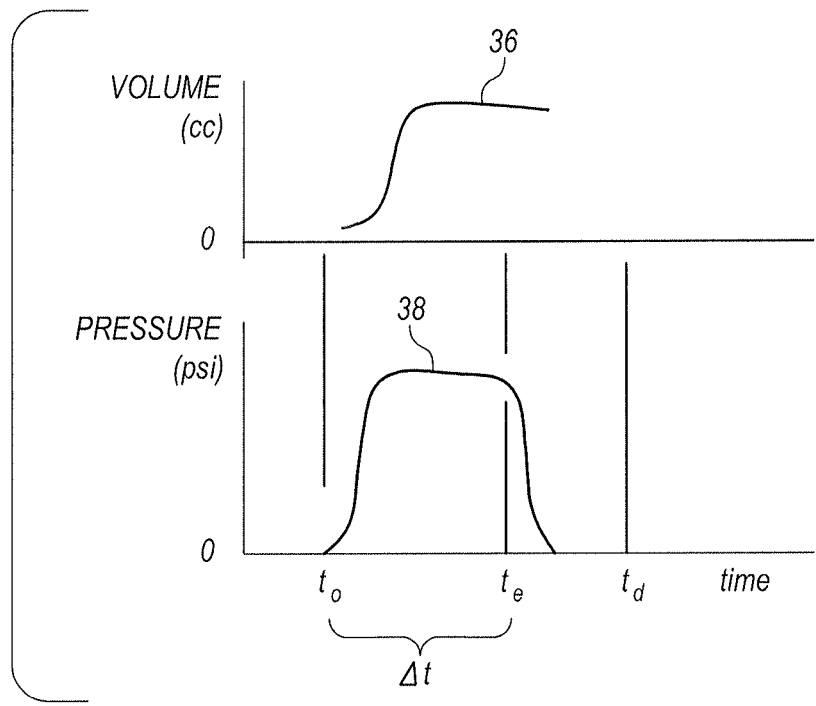
FIG. 4 is a balloon-volume and balloon-pressure time graph, depicting volume and pressure changes during the pre-ejection phase of a heart muscle pumping cycle.

Referring initially to FIG. 1, a system for improving a heart muscle response in accordance with the present invention is shown and is generally designated 10. As shown, the system 10 includes a computer 12, a pump 14 and a catheter 16. Further, a connector 18 is provided at the proximal end 20 of the catheter 16 for connecting the computer 12 and the pump 14 with the catheter 16.

As generally shown in FIG. 2, the distal end 22 of the catheter 16 includes an inflatable balloon 24 and a pressure transducer 26. For the present invention, the balloon 24 may be made of either a non-compliant material or, preferably, a compliant material. Also, the volume of the balloon 24, when it is completely inflated, will be in a range between 2 cc and 7 cc. FIG. 2 also shows that a pressure transducer 26 is located at the distal end 22 of the catheter 16. For the system 10, the pressure transducer 26 will be of a type that is capable of detecting pressure in a fluid, such as a Millar Mikro-Tip® pressure transducer.

In a combination of components for the system 10, the balloon 24 is connected in fluid communication with the pump 14 via a lumen 28 of the catheter 16 (see FIG. 3). Also, the pressure transducer 26 is electrically connected with the computer 12 via a wire 30 which is included with the catheter 16 (again, see FIG. 3). Additionally, it is to be noted that the computer 12 is electrically connected with the pump 14.

For an operation of the system 10, the distal end 22 of the catheter 16 is inserted into the left ventricle of a heart muscle 32 of a patient 34. With reference to FIG. 4 it is to be appreciated that both the inflation volume of the balloon 24, and the blood pressure that is detected by the pressure transducer 26 are detected simultaneously, and are respectively controlled/monitored by the computer 12. All of this is done, of course, while the distal end 22 of the catheter 16 is positioned in the left ventricle of the heart muscle 32. With the distal end 22 of the catheter 16 so positioned, the control and monitoring of a patient's 34 heart function by the computer 12 is envisioned to be continuous, and over a prolonged succession of pumping cycles by the heart muscle 32.

With the above in mind and referring to FIG. 4, a graph line 36 showing changes in the volume of balloon 24 as a function of time is presented. FIG. 4 also includes a graph line 38 showing variations in the pressure that is sensed by pressure transducer 26 as a function of time. Together, the changes in balloon volume (line 36) and the variations in pressure (line 38) are shown relative to the pre-ejection phase of a heart muscle 32 cycle, during the time interval $\Delta t$. Typically, $\Delta t$ will last approximately 10 msec ($\Delta t$=10 msec). In this context, a complete pumping cycle for a heart muscle 32 lasts approximately 500 msec.

With reference to FIG. 4 it will be seen that the predetermined interval $\Delta t$ for the pre-ejection phase of heart muscle 32 begins at a time $t_0$ and it ends at a time $t_e$. Importantly, during $\Delta t$ the pumping chamber 40 is full of blood, and it is enclosed (i.e. fluid tight). Also, at $t_0$ it happens naturally that the heart muscle 32 begins to contract, and thereby exert an isometric pressure on blood in the pumping chamber 40.

Figure 5A:
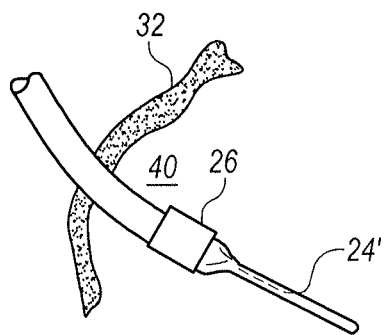
FIG. 5A is a view of the distal tip of the catheter when it has been inserted into the left ventricle pumping chamber of the heart and is generating isometric pressure in the pumping chamber during the pre-ejection phase of the heart muscle's pumping cycle.

It is an important aspect of the present invention that the isometric pressure on blood in the pumping chamber 40, beginning at time $t_0$, causes a sudden rise in pressure in the pumping chamber 40 (see line 38 in FIG. 4). This pressure is sensed by the pressure transducer 26, and the pressure rise is transferred as a predetermined signal to the computer 12 for activating the pump 14 to thereby inflate the balloon 24. With the activation of the pump 14, the volume increase of balloon 24' is also quite rapid (see line 36 in FIG. 4 and balloon 24' in FIG. 5A). Thus, the transition from the deflated balloon 24' (FIG. 5A) into a fully inflated balloon 24 (FIG. 5B) is almost immediate. The consequence of this is that during the time interval $\Delta t$ of the pre-ejection phase, pressure from pump 14 on the balloon 24'-24 creates an additional isometric pressure that supplements the natural isometric pressure from heart muscle 32 on blood in the pumping chamber 40.

Figure 5B:
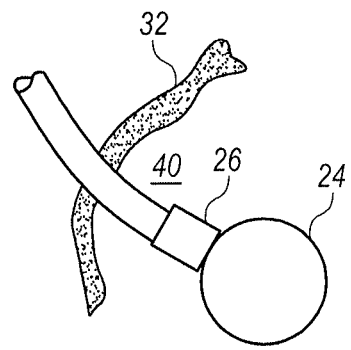
FIG. 5B is a view of the distal tip of the catheter as shown in FIG. 5A after the pre-ejection phase of the heart muscle's pumping cycle.

At time $t_e$, at the end of the pre-ejection phase, the outlet valve (not shown) from the pumping chamber 40 is opened. Blood is then pumped by the heart muscle 32 from the pumping chamber 40. Also, at the time $t_e$, with the ejection of blood from the pumping chamber 40, the balloon 24' is no longer constrained and it becomes fully inflated as seen in FIG. 5B. As shown by line 36 in FIG. 4, sometime after the pre-ejection phase has ended at $t_e$, the balloon 24 is deflated at a time $t_d$. This entire process is then repeated during the pre-ejection phase, in the next heart pumping cycle.

Figure 6:
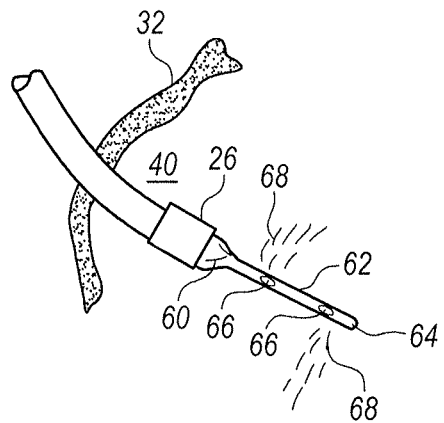
FIG. 6 is a view of an alternate embodiment for the distal tip of the catheter positioned in the left ventricle of the heart, wherein a hollow needle having an end cap and a plurality of lateral fluid ejection ports is used to inject a fluid into the left ventricle during the pre-ejection phase of the heart muscle's pumping cycle.

For an alternate embodiment of the system 10, instead of the balloon 24, an injection tube, generally designated 60 in FIG. 6, is used to increase isometric pressure in the pumping chamber 40 of the heart muscle 32 during the time of the pre-ejection phase, $\Delta t$. Structurally, the injection tube 60 essentially includes a hollow needle 62 which has an end cap 64 at its distal end. Additionally, the hollow needle 62 is formed with a plurality of lateral side ports 66 positioned along the length of the hollow needle 62 for ejecting fluid from the hollow needle 62.

In an operation of the alternate embodiment for the present invention, at the time $t_0$, the predetermined signal from the pressure transducer 26 to the computer 12 activates the pump 14 to inject a fluid from the injection tube 60 and into the pumping chamber 40 of the heart muscle 32. This action by the system 10, as similarly disclosed above for the inflatable balloon 24, introduces a fluid volume into the pumping chamber 40 that causes a supplemental increase in isometric pressure. As envisioned for the present invention, the volume of fluid injected will typically be in a range between 2 cc and 7 cc. In effect, the variations in volume and pressure that are shown in FIG. 4 are essentially the same during $\Delta t$ for the alternate embodiment (i.e. fluid injection) as was disclosed above for the preferred embodiment (i.e. balloon inflation).

For the alternate embodiment, the injection fluid 68 that is used may be either a standard saline solution, a plasma, or a hypo-tonic solution. As is well known by qualified medical personnel, each of the possible fluids 68 have both "pro" and "con" characteristics. In each instance, however, the amount of fluid 68 to be injected during the time $\Delta t$ of a pre-ejection phase will be approximately 2 cc. Thus, depending on the fluid 68 that is used, it may be necessary to inject fluid 68 from the injection tube 60 only during alternate heart pumping cycles, or during only every third or fourth heart pumping cycle.

Figure 7:
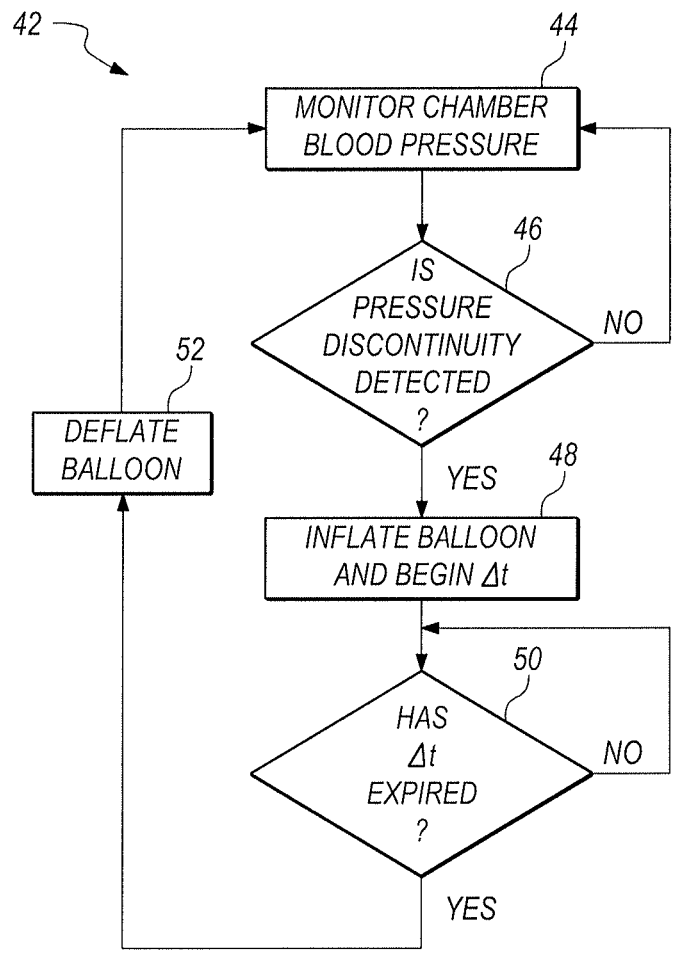
FIG. 7 is a logic flow chart of an operation of the computer during a clinical use of the present invention.

An operation of the system 10 will be best appreciated with reference to the logic flow chart 42 shown in FIG. 7. In FIG. 7, action block 44 indicates that an operation of the system 10 requires monitoring pressure on blood in the pumping chamber 40 of heart muscle 32. The operation is actually cyclical in nature, with each cycle beginning at a time $t_0$ when the pressure transducer 26 senses a sudden, abrupt rise in pressure on blood in the pumping chamber 40. From a mechanical perspective, this pressure rise (i.e. a pressure discontinuity) occurs at the time $t_0$ when the pumping chamber 40 has been filled with blood, and both the inlet valve (not shown) and the outlet valve (also not shown) of the pumping chamber 40 have closed. With the heart muscle 32 in this condition, at $t_0$ the heart muscle 32 tries to contract to thereby exert isometric pressure on blood in the pumping chamber 40. As indicated by inquiry block 46, this pressure increase at $t_0$ sends a signal from the pressure transducer 26 to the computer 12. In response to the signal, and as indicated by action block 48, computer 12 activates pump 14 to inflate the balloon 24 during the pre-ejection phase.

At time $t_e$, i.e. at the end of the pre-ejection phase, isometric pressure from the heart muscle 32, which has been supplemented by isometric pressure from the balloon 24, causes the outlet valve (not shown) of the heart muscle 32 to open. Blood is then ejected from the pumping chamber 40. Inquiry block 50 then directs the computer 12 to deflate the balloon 24 (see action block 52). As envisioned for the present invention, the operation of system 10 is repeated during a succession of heart pumping cycles, for an extended period of time that is determined by attending clinical personnel.

While the particular System and Method for Improving a Heart Muscle Response as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A system for improving heart muscle response during a pre-ejection phase in the heart muscle pumping cycle which comprises:

a catheter having a proximal end and a distal end;

a pressure transducer mounted on the catheter at the distal end thereof for measuring a blood pressure inside a pumping chamber of the heart muscle when the distal end of the catheter is inserted into the pumping chamber;

an inflatable balloon mounted on the catheter at the distal end thereof, wherein the inflatable balloon has a volume in a range between 2 cc and 7 cc when completely inflated;

a pump connected to the proximal end of the catheter in fluid communication with the inflatable balloon; and a computer connected with the pressure transducer and with the pump, to activate the pump in response to a predetermined signal from the pressure transducer, and to fully inflate the balloon and increase fluid volume in the pumping chamber with a predetermined volume of fluid during a predetermined time interval $\Delta t$ during the pre-ejection phase while the pumping chamber is isovolumic, wherein $\Delta t$ is approximately 10 msec, to assist contractile elements of the heart muscle in generating an isometric pressure in the pumping chamber, in preparation for a subsequent ejection of blood from the pumping chamber by series-elastic elements of the heart muscle in a post pre ejection phase.

2. The system as recited in claim 1 wherein the predetermined signal from the pressure transducer is an abrupt increase in pressure on blood inside the pumping chamber.

3. The system as recited in claim 1 wherein the system further comprises saline for use in inflating the balloon.

4. A method for improving heart muscle response during a pre-ejection phase in the heart muscle pumping cycle which comprises the steps of:
  providing a catheter having a proximal end and a distal end, with an inflatable balloon mounted on the catheter at the distal end thereof, wherein the inflatable balloon has a volume in a range between 2 cc and 7 cc when completely inflated, and a pressure transducer mounted on the catheter at the distal end thereof for measuring a blood pressure inside a pumping chamber of the heart muscle;
  inserting the distal end of the catheter into the pumping chamber;
  monitoring blood pressure in the pumping chamber with the pressure transducer;
  increasing a fluid volume in the pumping chamber by fully inflating the balloon in response to a predetermined signal from the pressure transducer to increase fluid volume in the pumping chamber with a predetermined volume of fluid during a predetermined time interval $\Delta t$ during the pre-ejection phase while the pumping chamber is isovolumic, wherein $\Delta t$ is approximately 10 msec, to assist contractile elements of the heart muscle in generating an isometric pressure in the pumping chamber during the pre-ejection phase, in preparation for a subsequent ejection of blood from the pumping chamber by series-elastic elements of the heart muscle in a post pre-ejection phase; and
  sequentially repeating the monitoring and increasing steps to improve heart muscle response.

5. The method as recited in claim 4 wherein the method further comprises the step of deflating the balloon after the pre-ejection phase.

6. The method as recited in claim 5 wherein saline is used for inflating the balloon.

7. The method as recited in claim 4 wherein the predetermined signal from the pressure transducer is an abrupt increase in pressure on blood inside the pumping chamber.

8. A non-transitory, computer-readable medium having executable instructions stored thereon that direct a computer system to perform a process for improving heart muscle response during a pre-ejection phase in the heart muscle pumping cycle, the medium comprising instructions for:
  monitoring blood pressure in a pumping chamber of the heart muscle with a pressure transducer;
  activating and fully inflating an inflatable balloon having a volume between 2 cc and 7 cc when completely inflated in response to a predetermined signal from the pressure transducer to increase fluid volume in the pumping chamber for a predetermined time interval $\Delta t$, to increase fluid volume in the pumping chamber with a predetermined volume of fluid during a predetermined time interval $\Delta t$ during the pre-ejection phase while the pumping chamber is isovolumic, wherein $\Delta t$ is approximately 10 msec, to assist contractile elements of the heart muscle in generating an isometric pressure in the pumping chamber during the pre-ejection phase, in preparation for a subsequent ejection of blood from the pumping chamber by series-elastic elements of the heart muscle in a post pre-ejection phase; and
  sequentially repeating the monitoring and activating instructions to improve heart muscle response.

9. The medium as recited in claim 8 wherein the medium further comprises an instruction for deflating the balloon after the pre-ejection phase, wherein saline is used for inflating the balloon.

10. The medium as recited in claim 8 wherein the predetermined signal from the pressure transducer is an abrupt increase in pressure on blood inside the pumping chamber.

\* \* \* \* \*

UNITED STATES PATENT AND TRADEMARK OFFICE
CERTIFICATE OF CORRECTION

PATENT NO. : 10,117,982 B2
APPLICATION NO. : 15/099975
DATED : November 6, 2018
INVENTOR(S) : Guy P. Curtis It is certified that error appears in the above-identified patent and that said Letters Patent is hereby corrected as shown below:

In the Claims

Column 8, Line 27 - after the word "interval" and before the word "during" DELETE "At" and INSERT -- $\Delta t$ --.

Signed and Sealed this
Fifth Day of February, 2019

Andrei Iancu
*Director of the United States Patent and Trademark Office*